United States Patent [19]

Antberg et al.

[11] Patent Number: 5,202,398

[45] Date of Patent: Apr. 13, 1993

[54] PROCESS FOR THE PREPARATION OF A 1-OLEFIN POLYMER

[75] Inventors: Martin Antberg; Hartmut Lüker, both of Hofheim am Taunus; Ludwig Böhm, Hattersheim am Main, all of Fed. Rep. of Germany

[73] Assignee: Hoechst Aktiengesellschaft, Frankfurt am Main, Fed. Rep. of Germany

[21] Appl. No.: 453,147

[22] Filed: Dec. 13, 1989

Related U.S. Application Data

[63] Continuation of Ser. No. 201,460, Jun. 2, 1988, abandoned.

[30] Foreign Application Priority Data

Jun. 5, 1987 [DE] Fed. Rep. of Germany ....... 3718888

[51] Int. Cl.$^5$ .................... C08F 4/656; C08F 4/655; C08F 10/00
[52] U.S. Cl. .................................. 526/129; 502/120; 526/127; 526/142
[58] Field of Search ................ 526/129, 160, 127, 142

[56] References Cited

U.S. PATENT DOCUMENTS

| | | | |
|---|---|---|---|
| 3,326,877 | 6/1967 | Orzechowski et al. | 526/129 |
| 3,635,935 | 1/1972 | Long | 526/129 |
| 3,738,944 | 6/1973 | Candlin et al. | 526/129 |

FOREIGN PATENT DOCUMENTS 206794 12/1986 European Pat. Off. .

Primary Examiner—Edward J. Smith

[57] ABSTRACT

If the transition metal component used in an olefin polymerization catalyst is the product of the reaction between a siloxane-substituted metallocene of titanium, zirconium or hafnium and a hydroxyl group-containing support material, for example silicon dioxide, these metallocene catalysts can be employed in existing polymerization plants which are designed for the suspension process.

12 Claims, No Drawings

PROCESS FOR THE PREPARATION OF A 1-OLEFIN POLYMER

This is a continuation of U.S. application Ser. No. 201,460, filed Jun. 2, 1988 now abn.

The present invention relates to a process for the preparation of a 1-olefin polymer using a supported metallocene catalyst.

Metallocenes of transition metals are known as catalyst components (cf. U.S. Pat. No. 4,522,982 and U.S. Pat. No. 4,542,199). Together with aluminoxanes, they form homogeneous transition metal catalysts which are soluble in aromatic hydrocarbons. These catalysts are very active. However, their solubility is a disadvantage if such catalysts are to be employed in existing industrial plants since the latter are generally designed for the use of heterogeneous catalyst systems. It was therefore desirable to find metallocene catalysts which can be used in the form of a suspension.

Metallocene catalysts in which a zirconocene or titanocene component and an aluminoxane are applied together from a solution onto a silicate support are known (cf. European Application Publication 206,794). However, this catalyst system is not very active and has the disadvantage that the ratio between Zr or Ti and Al cannot be changed during the polymerization. In addition, the catalyst components are not bound sufficiently strongly to the support and can thus be extracted from the hot suspending agent during the polymerization.

It has now been found that these disadvantages can be avoided if only the transition metal compound, in the form of a siloxane-substituted metallocene, is applied to the support.

The invention thus relates to the process described in the claims.

In order to prepare the transition metal component of the catalyst to be used according to the invention, a metallocene compound is reacted with a hydroxyl group-containing support material.

A metallocene compound of the formula (I)

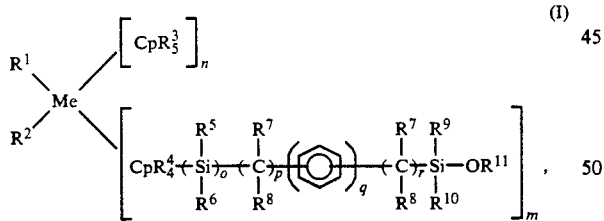

in which
Me is titanium, zirconium or hafnium, preferably zirconium, and
Cp denotes the cyclopentadienyl ring;
$R^1$ and $R^2$, independently of one another, are a hydrogen atom, a halogen atom, a $C_1$-$C_4$-alkyl group or a $C_6$-$C_{10}$-aryl group, preferably an alkyl group or a halogen atom, in particular a chlorine atom;
$R^3$ and $R^4$, independently of one another, denote a hydrogen atom, a halogen atom, a $C_1$-$C_4$-alkyl group, a $C_1$-$C_4$-alkoxy group, a $C_6$-$C_{10}$-aryl group or a $C_2$-$C_6$-alkenoxy group, preferably a hydrogen atom or methyl, in particular a hydrogen atom;
$R^5$ and $R^6$, independently of one another, are a $C_1$-$C_4$-alkyl group, a $C_6$-$C_{10}$-aryl group or a $C_1$-$C_4$-alkoxy group, preferably an alkyl group, in particular methyl;
$R^7$ and $R^8$, independently of one another, are a hydrogen atom, a $C_1$-$C_4$-alkyl group or a $C_6$-$C_{10}$-aryl group, preferably an alkyl group or a hydrogen atom, in particular a hydrogen atom;
$R^9$ and $R^{10}$, independently of one another, denote a $C_1$-$C_4$-alkyl group, a $C_6$-$C_{10}$-aryl group or a $C_1$-$C_4$-alkoxy group, preferably an alkyl group, in particular methyl;
$R^{11}$ is a $C_1$-$C_4$-alkyl group, preferably ethyl;
m denotes 1 or 2, preferably 1,
n is 2 - m,
o is zero or 1, preferably 1,
p is a number from zero to 6, preferably 1,
q is zero or 1, preferably zero, and
r is a number from zero to 6, preferably 1, is used.

Examples of suitable metallocene compounds of the formula (1) are

1. 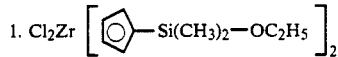

2. 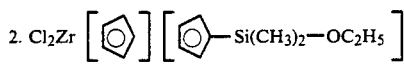

3. 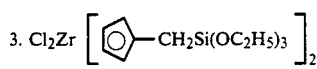

4. 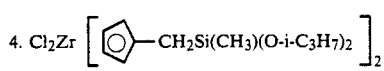

5. 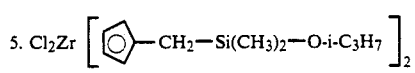

6. 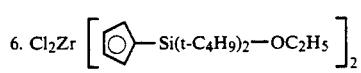

7. 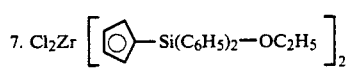

8. 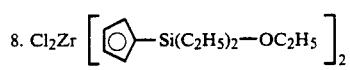

9. 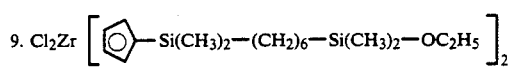

10. 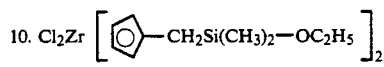

11. 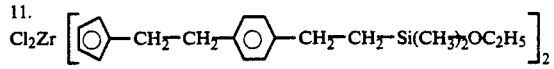

12. 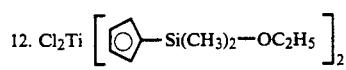

13. 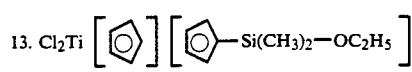

14. Cl₂Hf 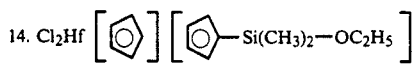

Of these compounds, preferred compounds are Nos. 1, 2, 3 and 4, in particular No. 2.

Compounds of this type are described in I. B. L. Booth, G. C. Ofume, C. Stacey and P. J. T. Tait in J. Organomet. Chem. 315 (1986), pp. 143-156, and R. Jackson, J. Ruddlesden, D. J. Thomson and R. Whelan in J. Organomet, Chem. 125 (1977), pp. 57-62.

Suitable support materials are inorganic oxides, carbonates such as chalk, silicates such as talc, and polymers having hydroxyl groups at the surface. Particularly suitable supports are porous oxides or mixed oxides of silicon and/or aluminum which have a specific surface area of 50 to 1,000 m²/g, preferably 100 to 800, in particular 150 to 650, and whose pore volume is in the range 0.2 to 3, preferably 0.4 to 3, in particular 0.6 to 2.7, cm³/g. The particle size is 1 to 500 μm, preferably 10 to 200 μm, in particular 20 to 100 μm. Depending on the specific surface area and the temperature pretreatment, the hydroxyl group number is in the range 0.5 to 50 mmol, preferably 1 to 20, in particular 1.5 to 10, hydroxyl groups per gram of support. Some such oxides are prepared specifically for use as supports for supporting catalysts and are commercially available.

Before reacting the support with the metallocene compound, it is necessary to remove adsorptively bound water by drying at a temperature from 120° to 800° C., preferably 200° to 500° C., which may take 1 to 10 hours. The drying is monitored analytically by titrating the OH content of the support material against n-butylmagnesium chloride. After drying, the support is stored under an inert gas, for example nitrogen or argon, with exclusion of air and water.

The support is reacted with the metallocene compound by suspending the support in the inert solvent and heating the dissolved metallocene compound at a temperature of 0° to 40° C., preferably 15° to 25° C., for 1 to 1,260 minutes, preferably 20 to 180 minutes. The ratio between the metallocene compound and the support is chosen as a function of the hydroxyl group content so that 10 to 400, preferably 200 to 250, mmol of metallocene compound are employed per 100 grams of support.

Suitable solvents are all solvents which can be used for olefin polymerization, thus, for example, aliphatic or cycloaliphatic hydrocarbons, for example pentane, hexane, heptane, cyclohexane and methylcyclohexane, aromatic hydrocarbons, such as benzene, toluene, xylene and/or petroleum or hydrogenated diesel oil fractions which have been carefully freed from oxygen, sulfur compounds and moisture. Aliphatic and cycloaliphatic hydrocarbons are preferably used.

The second component of the catalyst according to the invention is an aluminoxane of the formula (II)

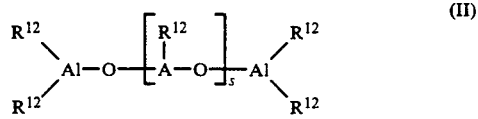

for the linear type and/or of the formula (III)

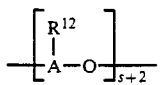

for the cyclic type. In these formulae, $R^{12}$ denotes a $C_1$-$C_6$-alkyl group, preferably methyl, ethyl or isobutyl, in particular methyl, and s denotes an integer from 2 to 40, preferably 10 to 20.

The aluminoxane can be prepared in various ways.

In one of the processes, finely powdered copper sulfate pentahydrate is slurried in toluene, and sufficient aluminum trialkyl so that about 1 mole of $CuSO_4.5H_2O$ is available for each 4 Al atoms is added at about −20° C. in a glass flask under an inert gas. After slow hydrolysis with elimination of alkane, the reaction mixture is left at room temperature for 24 to 48 hours, cooling possibly being necessary so that the temperature does not exceed 30° C. The copper sulfate is subsequently filtered off from the aluminoxane dissolved in the toluene, and the toluene is removed by vacuum distillation. It is assumed that, in this preparation process, the low-molecular-weight aluminoxanes condense to form higher oligomers with elimination of aluminum trialkyl.

Furthermore, aluminoxanes are obtained when aluminum trialkyl, preferably aluminum alkyl, dissolved in an inert aliphatic or aromatic solvent, preferably heptane or toluene, is reacted with aluminum salts, preferably aluminum sulfate, containing water of crystallization, at a temperature of −20° to 100° C. The ratio by volume between the solvent and the aluminum alkyl used is 1:1 to 50:1, preferably 5:1, and the reaction time, which can be monitored by the elimination of alkane, can be 1 to 200 hours, preferably 10 to 40 hours.

Of the aluminum salts containing water of crystallization, those are used in particular which have a high content of water of crystallization. Aluminum sulfate hydrate is particularly preferred, above all the compounds $Al_2(SO_4)_3.18H_2O$ and $Al_2(SO_4)_3.16H_2O$ having the particularly high content of water of crystallization of 18 or 16 moles of $H_2O$ per mole of $Al_2(SO_4)_3$.

The catalyst to be used according to the invention is employed for polymerization of 1-olefins of the formula R—CH=CH₂ in which R is hydrogen or a straight-chain or branched alkyl radical having 1 to 12 carbon atoms, preferably 1 to 6 carbon atoms, for example ethylene, propylene, 1-butene, 1-hexene, 4-methyl-1-pentene or 1-octene. Ethylene and propylene are particularly preferred.

The polymerization is carried out in a known manner in suspension or in the gas phase, continuously or batchwise, in one step or in a number of steps, at a temperature of 0° to 100° C., preferably 70° to 90° C. The pressure is 0.5 to 64 bar. The polymerization is preferred in the industrially particularly important pressure range 5 to 64 bar.

In the polymerization, the transition metal component is used in a concentration, relative to the transition metal, of $10^{-3}$ to $10^{-6}$, preferably $10^{-4}$ to $10^{-6}$, moles of Ti, Zr or Hf per liter of solvent or per liter of reactor volume. The aluminoxane is used in a concentration of $10^{-4}$ to $10^{-1}$, preferably $10^{-3}$ to $2\times10^{-2}$, moles per liter of solvent or per liter of reactor volume, relative to the content of aluminum. In principle, however, higher concentrations are also possible.

The polymerization is carried out in an inert solvent which is customary for the Ziegler low-pressure process, for example in an aliphatic or cycloaliphatic hydrocarbon; butane, pentane, hexane, heptane, isooctane, cyclohexane and methylcyclohexane may be mentioned as examples of such solvents. It is also possible to use a petroleum or hydrogenated diesel oil fraction which has been carefully freed from oxygen, sulfur compounds and moisture. Toluene can also be used. Finally, it is also possible to employ the monomers to be polymerizaed as solvents or suspending agents. The molecular weight of the polymer can be regulated in a known fashion; hydrogen is preferably used for this purpose.

The catalyst to be used according to the invention is distinguished by the fact that the transition metal compound is strongly bound to the support material. It has been possible to show that alcohol is formed during the reaction of the metallocene compound with the support material, for example in accordance with the following equation:

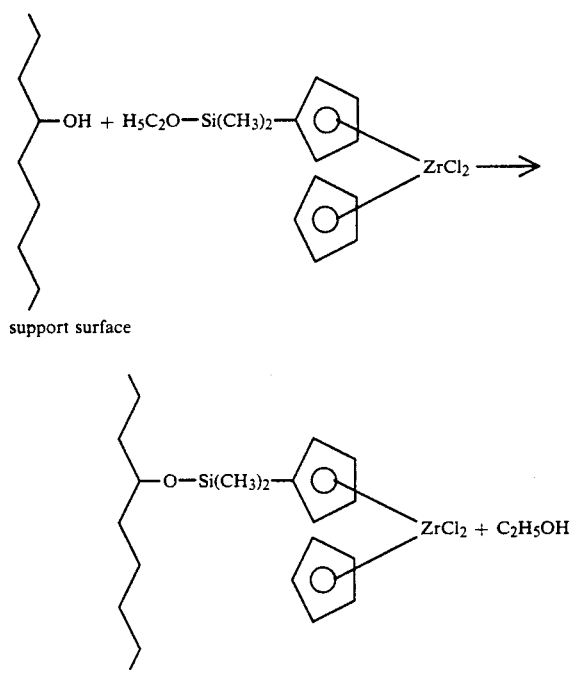

support surface

Extremely high yields are achieved with the aid of the catalyst to be used according to the invention.

The following Examples are intended to illustrate the invention.

EXAMPLE 1

Preparation of a Preferred Metallocene

Cyclopentadienyl[(dimethylethoxysilyl)cyclopentadienyl]-zirconium dichloride 9.36 g (43.35 mmol) of potassium dimethylethoxysilylcyclopentadienide in 30 cm$^3$ of tetrahydrofuran were added dropwise at $-50°$ C. to a suspension of 11.3 g (43.02 mmol) of cyclopentadienylzirconium trichloride in 100 cm$^3$ of tetrahydrofuran within 1 hour. After stirring at $-20°$ C. for 2 hours, the batch was warmed to room temperature and stirring was continued overnight. The batch was filtered, the filtrate was evaporated, and the residue was extracted with pentane. White needles crystallized from the filtered and concentrated pentane extract on cooling and were separated off, washed with cold pentane and dried in vacuo.

Yield 3.75 g (7.55 mmol = 34% of theory)

Elemental analysis and $^1$H NMR spectrum were consistent with the structure given above.

EXAMPLE 2

5.47 g of silicon dioxide (0.88 mmol of OH groups/g) were suspended in 30 cm$^3$ of toluene. 0.9 g (2.28 mmol) of Cl$_2$Zr(C$_5$H$_5$)(C$_5$H$_4$—Si(CH$_3$)$_2$—OC$_2$H$_5$), dissolved in 20 ml of toluene, was added at 0° C. over 15 minutes. When the batch had warmed to room temperature, it was stirred for a further 14 hours. The solid was separated off, washed three times with 20 cm$^3$ of diethyl ether in each case and dried in vacuo. In order to remove metallocene which was not chemically bound, the solid was extracted for 24 hours in a Soxhlet apparatus using benzene and subsequently dried in a high vacuum. Zr content 2.7% by weight.

EXAMPLE 3

750 cm$^3$ of a diesel oil fraction (b.p. 100° to 120° C.) were introduced into a 1 dm$^3$ polymerization reactor and heated to 70° C. The reactor was charged with 6.4 cm$^3$ of a methyl aluminoxane solution containing 0.22 mmol of aluminum, and with 67 mg (0.02 mmol of Zr) of the transition metal component from Example 2 in 10 cm$^3$ of solvent. Ethylene was then passed in to a final pressure of 7 bar and polymerized for 1 hour. 60.6 g of polyethylene corresponding to 3.05 mmole of Zr×h, were obtained. The product obtained had the following data:

| MFI 190/21.6 | 0.09 g/10 min |
|---|---|
| Viscosity No. | 600 cm$^3$/g |
| Density | 0.946 g/cm$^3$. |

EXAMPLE 4

The procedure carried out was as in Example 3, but the amount of transition metal component used was now 0.01 mmol, relative to zirconium.

| Yield | 42 g; MFI 190/21.6 | 0.09 g/10 min |
|---|---|---|
| Viscosity No. | 600 cm$^3$/g | |
| Density | 0.946 g/cm$^3$ | |
| Catalyst yield | 4.2 kg/mmol | |

EXAMPLE 5

The procedure carried out was as in Example 3, but 9.8 cm$^3$ of 1-butene (106 mmol) were introduced into the reactor after addition of the catalyst components and the ethylene pressure was subsequently restored to 7 bar.

| Yield | 36 g; MFI 190/21.6 | 0.15 g/10 min |
|---|---|---|
| Viscosity No. | 400 cm$^3$/g | |
| Density | 0.942 g/cm$^3$ | |
| Catalyst yield | 1.8 kg/mmol | |

COMPARATIVE EXAMPLE A

The yield was calculated from the data in EP 206,794 (Example 1); it is considerably below the level of the examples according to the invention.

| | |
|---|---|
| Zirconium concentration (mmol) | 0.034 |
| Aluminum concentration (mmol of Al) | 0.83 |
| Aluminum:zirconium (mol:mol) | 24.4 |
| Ethylene pressure (bar) | 13.8 |
| Temperature (°C.) | 85 |
| Yield (kg) | 0.0123 |
| Catalyst yield (kg/mmol of Zr) | 0.36 |

EXAMPLE 6

The procedure carried out was as in Example 3, but the Zr transition metal component was replaced by the analogous Ti component in an amount of 40 mg (0.02 mmol of Ti). The Ti content of the component was 2.4% by weight.

| | |
|---|---|
| Yield | 28 g of PE, corresponding to a calculated yield of 1.4 kg of PE/mmol of Ti. |
| MFI 190° C./21.6 | 0.07 g/10 min |
| Viscosity number | 720 cm³/g |
| Density | 0.948 g/cm³ |

EXAMPLE 7

The procedure carried out was as in Example 3, but the Zr transition metal component was replaced by the analagous Hf component in an amount of 137 mg (0.02 mmol of Hf). The Hf content of the component was 2.6% by weight.

| | |
|---|---|
| Yield | 12 g of PE, corresponding to a catalyst yield of 0.6 kg of PE/mmol of Hf. |
| MFI 190° C./21.6 | 0.06 g/10 min |
| Viscosity number | 810 cm³/g |
| Density | 0.947 g/cm³ |

We claim:

1. In a process for the preparation of 1-olefin polymer by polymerizing a 1-olefin of the formula R—CH=CH$_2$ in which R is hydrogen or a straight-chain or branched alkyl group having 1 to 12 carbon atoms, at a temperature of −60° to 100° C., at a pressure of 0.5 to 64 bar, in suspension or in the gas phase, in the presence of a catalyst which comprises a transition metal component and an aluminoxane, the improvement comprising carrying out the polymerization in the presence of a catalyst whose transition metal component has been prepared by reacting a metallocene compound with a support material having hydroxyl groups reactive with at least one chemical moiety provided on the metallocene, said metallocene compound having the formula I $$\underset{R^2}{\overset{R^1}{\diagdown}}\mathrm{Me}\underset{}{\overset{[CpR_5{}^3]_n}{\diagup}}\left[CpR_4{}^4\!\!-\!\!\underset{R^6}{\overset{R^5}{\underset{|}{\overset{|}{Si}}}}\!\!\!{\fbox{$o$}}\!\!-\!\!\underset{R^8}{\overset{R^7}{\underset{|}{\overset{|}{C}}}}\!\!{\fbox{$p$}}\!\!-\!\!{\fbox{\phantom{X}}}_q\!-\!\!\underset{R^8}{\overset{R^7}{\underset{|}{\overset{|}{C}}}}\!\!{\fbox{$r$}}\!\!\underset{R^{10}}{\overset{R^9}{\underset{|}{\overset{|}{Si}}}}\!\!-\!\!OR^{11}\right]_m \quad \text{(I)}$$

in which
Me is titanium, zirconium or hafnium,
Cp denotes the cyclopentadienyl ring, R$^1$ and R$^2$, independently of one another, denote a hydrogen atom, a halogen atom, a C$_1$-C$_4$-alkyl group or a C$_6$-C$_{10}$-aryl group, R$^3$ and R$^4$, independently of one another, denote a hydrogen atom, a halogen atom, a C$_1$-C$_4$-alkyl group, a C$_1$-C$_4$-alkoxy group, a C$_6$-C$_{10}$-aryl group or a C$_2$-C$_6$-alkenoxy group, R$^5$ and R$^6$, independently of one another, denote a C$_1$-C$_4$-alkyl group, a C$_6$-C$_{10}$-aryl group or a C$_1$-C$_4$-alkoxy group, R$^7$ and R$^8$, independently of one another, denote a hydrogen atom, a C$_1$-C$_4$-alkyl group or a C$_6$-C$_{10}$-aryl group, R$^9$ and R$^{10}$, independently of one another, denote a C$_1$-C$_4$-alkyl group, a C$_6$-C$_{10}$-aryl group or a C$_1$-C$_4$-alkoxy group, R$^{11}$ denotes a C$_1$-C$_4$-alkyl group,
m is 1 or 2,
n is 2 - m,
o is zero or 1,
p is a number from zero to 6,
q is zero or 1, and
r is a number from zero to 6, and wherein the aluminoxane is one for the formula II $$\underset{R^{12}}{\overset{R^{12}}{\diagdown}}\mathrm{Al}\!-\!\mathrm{O}\!-\!\!\left[\underset{|}{\overset{R^{12}}{\overset{|}{A}}}\!-\!\mathrm{O}\right]_s\!\!-\!\mathrm{Al}\underset{R^{12}}{\overset{R^{12}}{\diagup}} \quad \text{(II)}$$

for the linear type and/or of the formula (III)

$$-\!\!\left[\underset{|}{\overset{R^{12}}{\overset{|}{A}}}\!-\!\mathrm{O}\right]_{s+2}\!\!- \quad \text{(III)}$$

for the cyclic type, where, in the formulae II and III, R$^{12}$ denotes a C$_1$-C$_6$-alkyl group and s is an integer from 2 to 40.

2. The process as claimed in claim 1, wherein the transition metal component used is the product of the reaction between a metallocene compound of the formula (I) in which Me is titanium or zirconium, and a metal oxide.

3. The process as claimed in claim 2, wherein the transition metal component is the product of the reaction between a zirconium compound of the formula (I) and silicon dioxide.

4. The process as claimed in claim 1, wherein, in said compound of formula I, o, p, and q are all zero; r is zero or 1, R$^7$ and R$^8$ are hydrogen atoms; R$^9$ and R$^{10}$ are CH$_3$—, C$_2$H$_5$O—, or i—C$_3$H$_7$O—; and R$^{11}$ is C$_2$H$_5$— or C$_3$H$_7$—.

5. The process as claimed in claim 4, wherein said hydroxyl-group containing support material is a metal oxide.

6. The process as claimed in claim 4, wherein said hydroxyl-group containing support material is silicon dioxide.

7. The process as claimed in claim 6, wherein, in said compound of formula I, R$^3$ and R$^4$ are hydrogen atoms.

8. In a process for the polymerization of a 1-olefin polymer by polymerizing a 1-olefin at a temperature between −60 and 100 degrees C. at a pressure of 0.5 to 64 bar in suspension or in the gas phase, in the presence of a catalyst which comprises a transition metal component and a linear or cyclic aluminoxane, the improvement comprising:

carrying out the polymerization using a supported transition metal component consisting of cyclopentadienyl[dimethylethoxysilyl)cyclopentadienyl]zirconium dichloride, said metal component being provided on a support material having hydroxyl groups reactive with the metal component by reacting the metal component with the support material in an inert solvent and thereafter recovering the support as a solid substantially free of unbound metal component, and carrying out said polymerization using said supported metal component in the presence of said aluminoxane.

9. The process of claim 8 wherein the amount of said metal component reacted with the solid support is chosen as a function of the hydroxyl group content of the support.

10. The process of claim 8 wherein the support material is selected from inorganic oxides, carbonates, silicates and polymers having reactive hydroxyl groups at the surface.

11. The process of claim 10 wherein the support is a porous oxide of silicon or aluminum.

12. The process of claim 11 wherein the support is silicon dioxide.

* * * * *